United States Patent [19]
Baker

[11] Patent Number: 5,489,022
[45] Date of Patent: Feb. 6, 1996

[54] ULTRAVIOLET LIGHT ABSORBING AND TRANSPARENT PACKAGING LAMINATE

[75] Inventor: Brett O. Baker, Ellettsville, Ind.

[73] Assignee: Sabin Corporation, Bloomington, Ind.

[21] Appl. No.: 229,827

[22] Filed: Apr. 19, 1994

[51] Int. Cl.$^6$ ............................ A61R 17/06; B65B 55/02
[52] U.S. Cl. ............................ 206/439; 53/425; 206/489; 428/35.4; 428/421; 428/913
[58] Field of Search ..................... 206/439, 438, 206/484; 428/35.4, 36.6, 36.7, 412, 913, 421, 40; 53/425, 434

[56] References Cited

U.S. PATENT DOCUMENTS

| | | |
|---|---|---|
| 3,660,192 | 5/1972 | Smith et al. . |
| 3,926,311 | 12/1975 | Laske . |
| 4,064,314 | 12/1977 | McKenzie .................. 428/913 X |
| 4,150,744 | 4/1979 | Fennimore .................. 206/439 X |
| 4,177,620 | 12/1979 | Daly et al. ................... 53/425 |
| 4,206,844 | 6/1980 | Thukamoto et al. . |
| 4,242,414 | 12/1980 | McKenzie .................. 428/913 X |
| 4,264,656 | 4/1981 | Reeder . |
| 4,284,751 | 8/1981 | Hutt et al. . |
| 4,378,392 | 3/1983 | Segel ................................ 428/40 |
| 4,444,826 | 4/1984 | Sasaki et al. ................ 428/421 X |
| 4,484,970 | 11/1984 | Burzlaff et al. . |
| 4,581,072 | 4/1986 | Laity . |
| 4,661,566 | 4/1987 | Pruett et al. . |
| 4,680,335 | 7/1987 | Chambers et al. . |
| 4,728,712 | 3/1988 | Singh et al. . |
| 4,808,452 | 2/1989 | McShane . |
| 4,836,647 | 6/1989 | Beard . |
| 4,851,166 | 7/1989 | Kendall . |
| 4,854,734 | 8/1989 | Anderson . |
| 4,856,261 | 8/1989 | Hackett et al. . |
| 4,872,553 | 10/1989 | Suzuki et al. ............... 206/438 X |
| 4,893,898 | 1/1990 | Beard . |
| 4,910,942 | 3/1990 | Dunn et al. ..................... 53/425 |
| 4,954,393 | 9/1990 | Jones . |
| 4,960,637 | 10/1990 | Biczenczuk . |
| 4,998,400 | 3/1991 | Suzuki et al. .................. 53/425 |
| 5,026,610 | 6/1991 | Harrison . |
| 5,028,480 | 7/1991 | Dean . |
| 5,064,579 | 11/1991 | Kendall et al. . |
| 5,077,096 | 12/1991 | Sharaby . |
| 5,079,072 | 1/1992 | Christopherson . |
| 5,084,360 | 1/1992 | Young . |
| 5,085,943 | 2/1992 | Crighton et al. . |
| 5,108,810 | 4/1992 | Williams . |
| 5,116,407 | 5/1992 | Hunter et al. . |
| 5,192,603 | 3/1993 | Slater et al. . |
| 5,218,055 | 6/1993 | Marrion et al. . |
| 5,223,314 | 6/1993 | Watanabe et al. ................ 428/35.4 |
| 5,236,493 | 8/1993 | Hunter et al. . |
| 5,244,670 | 9/1993 | Upson et al. . |
| 5,246,659 | 9/1993 | Crighton et al. . |
| 5,322,161 | 6/1994 | Shichman et al. . |

FOREIGN PATENT DOCUMENTS

| | | |
|---|---|---|
| 0307173 | 3/1989 | European Pat. Off. . |
| 2461584 | 2/1981 | France . |
| 2051672 | 1/1981 | United Kingdom . |

OTHER PUBLICATIONS

Courtaulds Performance Films, "Dyed Polyester Films" Sales Brochure, 1990.

*Primary Examiner*—Bryon P. Gehman
*Attorney, Agent, or Firm*—Richard J. Godlewski

[57] ABSTRACT

A transparent packaging laminate (10) for use in a container (15) for protecting medical products (18) from oxidation and deterioration as a result of exposure to ultraviolet light. The laminate includes a first transparent film (11) of a polyethylene material laminated with a polyester adhesive (13) to a second transparent film (12) of a polyester material. The transparent polyethylene material has a water vapor transmission rate of less than 20 grams/m$^2$/24 hours. The transparent polyester material absorbs ultraviolet light having a wavelength in a range of from 285 to 358 nanometers and has a water vapor transmission rate greater than 20 grams/m$^2$/24 hours, whereby the resulting laminate is unexpectedly wrinkle-free after ethylene oxide sterilization. The container comprises the ultraviolet light absorbing laminate and a sheet of spun-bonded olefin material attached to the laminate, which is opaque to ultraviolet light and forms a cavity (17) therebetween with the laminate for containing a medical product therein.

36 Claims, 2 Drawing Sheets

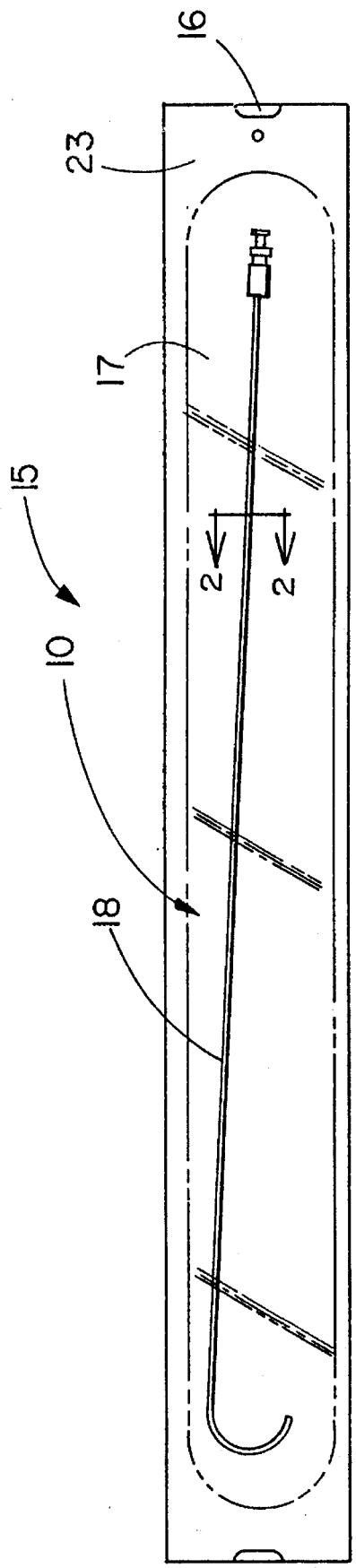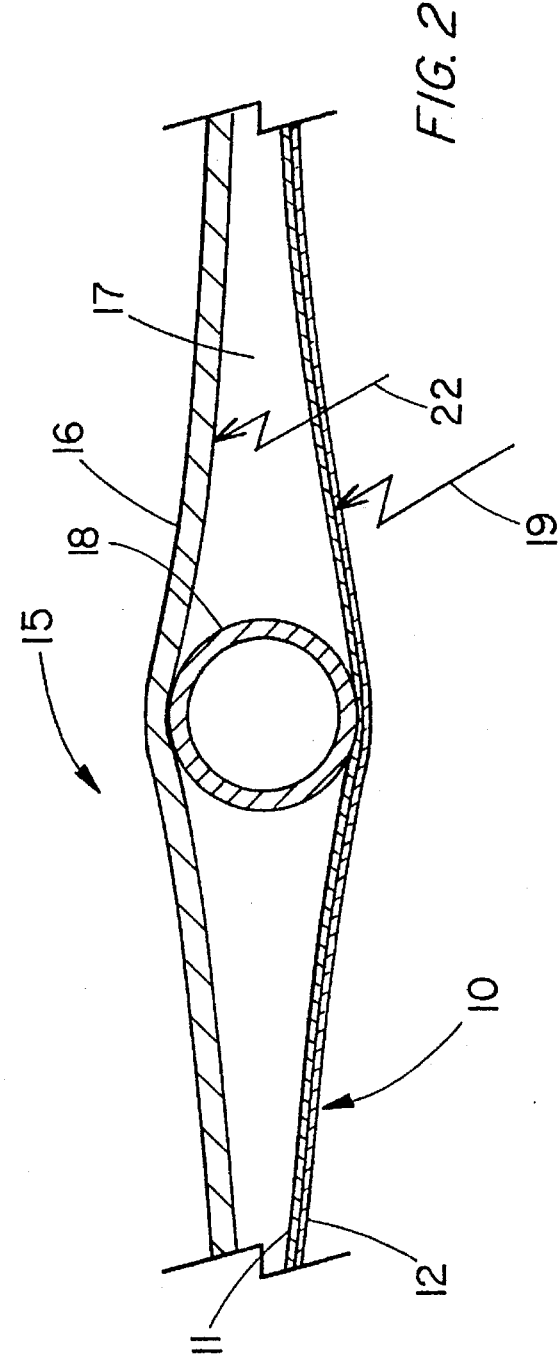

ULTRAVIOLET LIGHT ABSORBING AND TRANSPARENT PACKAGING LAMINATE

TECHNICAL FIELD

This invention relates generally to transparent packaging laminates and, in particular, to an ultraviolet light absorbing, transparent packaging laminate for use as a medical product container.

BACKGROUND OF THE INVENTION

Medical products such as plastic material catheters and the like are vulnerable to ultraviolet light oxidation and deterioration. One approach to combatting the effects of ultraviolet light on medical products is to include antioxidant and/or inhibitor additives in, for example, the material used to form plastic catheters. The antioxidants and/or inhibitors serve to extend the shelf life of ultraviolet light sensitive medical products. A problem with the use of antioxidants and/or inhibitors in catheter materials is that the resulting catheters exhibit undesirable characteristics such as increased durometer and stiffness. Furthermore, a high concentration of antioxidants and/or inhibitors negatively affects the bonding properties of constituent materials. Poor bonding of constituent materials can result in medical product failure, which impacts safety and efficacy for the patient.

Another approach to combatting the effects of ultraviolet light on medical products is to package a medical product in a container that is impervious to ultraviolet, as well as visible, light. Medical products are typically packaged in a pathogen-free environment or sterilized after packaging. A disadvantage of packaging medical products in a light-impervious container is that medical personnel are unable to visually identify the medical product before opening the container. As a result, medical products can be unnecessarily opened and exposed to an infectious environment.

SUMMARY OF THE INVENTION

The foregoing problems are solved and a technical advance is achieved in a medical package or container for a medical device which is adversely affected by a given range of wavelengths of ultraviolet light. The medical package or container comprises a pair of thermoplastic sheets at least one of which has a transparent portion which is capable of absorbing ultraviolet light at least in the given range of wavelengths and a remainder of the thermoplastic sheets is opaque at least to ultraviolet light in the given range of wavelengths. At least one of the thermoplastic sheets has at least a portion which is permeable to ethylene oxide gas and water vapor. A medical device which is adversely affected by the given range of wavelengths of ultraviolet light is positioned between the thermoplastic sheets so that it is visible through the transparent portion. A hermetic seal is provided between the thermoplastic sheets around all of the medical device, the transparent portion and around the permeable portion to hermetically encapsulate the medical device between the pair of thermoplastic sheets to thereby form a package with the medical device visible through the transparent portion. The interior of the package, including the medical device, is sterile, preferably by passing ethylene oxide and water vapor through the permeable portion of the package. At least the permeable portion of the thermoplastic sheets has a residual ethylene oxide content of less than 250 ppm.

Further according to the invention, there is provided an illustrative ultraviolet light absorbing, transparent packaging laminate for use as a medical product container and for advantageously protecting the product from oxidation and deterioration as a result of exposure to harmful ultraviolet light. In addition, the transparent laminate and container are advantageously suited for sterilizing a medical product contained therein with a commonly used sterilant such as ethylene oxide. The laminate and container along with the medical product therein also advantageously exhibit residuals of ethylene oxide less than 250 parts per million after ethylene oxide sterilization. Unexpectedly, the laminate with a constituent film having a high water vapor transmission rate exhibits a substantially wrinkle-free texture while maintaining its transparent property. The laminate also advantageously absorbs ultraviolet light having a wavelength in a given range of, for example, from 285 to 358 nanometers, which causes oxidation and deterioration of most medical products such as plastic material catheters and the like. Furthermore, medical products such as pharmaceuticals are also advantageously protected from deterioration due to harmful ultraviolet light in this wavelength spectrum.

The preferred transparent packaging laminate comprises a first transparent film of a synthetic polymer material and a second transparent film of an ultraviolet light absorbing polyester material laminated together with a polyester adhesive. The synthetic polymer material has a thickness of approximately 0.038 mm and a water vapor transmission rate of less than 20 grams/$m^2$/24 hours. The ultraviolet light absorbing polyester material absorbs ultraviolet light having a wavelength in a range of from 285 to 358 nanometers and has a thickness of approximately 0.013 mm and a water vapor transmission rate in excess of 20 grams/$m^2$/24 hours. The high water vapor transmission rate of the polyester material would suggest wrinkling thereof during the high humidity ethylene oxide sterilization process. However, the laminating of the transparent films unexpectedly results in laminate that is substantially wrinkle-free after ethylene oxide sterilization. In addition, the resulting laminate advantageously exhibits residuals of ethylene oxide below 250 ppm as required by the Federal Food and Drug Administration.

The synthetic polymer material is from a group of transparent polymeric materials which include polyvinylidene chloride, styrene, polyamides, polyether block amides, polyesters, and polyolefins. The styrene includes a butadiene styrene. The polyamides and polyether block amides include an ionomer film laminated thereto and formed from ethylene copolymers with methacrylic acid. The polyester polymeric material includes at least one of polyesterterephthalate and polyesterterephthalate glycol modified. The polyolefins include at least one of polyethylene and ethylene vinyl acetate.

The ultraviolet light absorbing medical product container comprises the ultraviolet light absorbing laminate and a sheet of spun-bonded olefin material attached to the laminate. The sheet of olefin material is opaque to ultraviolet light and forms a cavity between the transparent laminate for containing the medical product therein. The sheet of spun-bonded olefin readily transmits ethylene oxide gas and water vapor therethrough during the sterilization process, but blocks the transmission of harmful particulate such as bacteria, spores, and the like.

Further according to the invention, a method for packaging a medical device which is adversely affected by a given range of wavelengths of ultraviolet light comprises the steps of placing a medical device between a pair of thermoplastic sheets, at least one of which has a transparent portion which is capable of absorbing ultraviolet light at least in the given range of wavelengths and the remainder of the thermoplastic sheets is opaque at least to ultraviolet light in the given range of wavelengths. At least one of the thermoplastic sheets has at least a portion which is permeable to ethylene oxide gas and water vapor and is characterized by a residual ethylene oxide content of less than 250 ppm after sterilization. The thermoplastic sheets are hermetically sealed around all of the medical device, the transparent portion and the permeable portion to hermetically encapsulate the medical device between the pair of thermoplastic sheets to thereby form a package with the medical device visible through the transparent portion. Ethylene oxide and water vapor are then passed through the permeable portion to sterilize the medical device within the package and to sterilize the interior of the package. The ethylene oxide gas is subsequently removed from the package.

Preferably, one of the thermoplastic sheets comprises a first transparent thermoplastic film which has a water vapor transmission rate of at least 20 grams/m$^2$/24 hours and a second transparent thermoplastic film which is laminated to the first transparent film and is formed of an ultraviolet light absorbing polyester material having a water vapor transmission rate greater than 20 grams/m$^2$/24 hours. In accordance with a preferred embodiment of the invention, the other of the thermoplastic sheets is a spun-bonded olefin and the permeable portion comprises the spun-bonded olefin sheet.

BRIEF DESCRIPTION OF THE DRAWING

FIG. 1 depicts an illustrative embodiment of an ultraviolet light absorbing container of the present invention for containing medical products;

FIG. 2 depicts a partially enlarged cross-sectional view of the container of FIG. 1 taken along the line 2—2;

DETAILED DESCRIPTION

Figure 3:
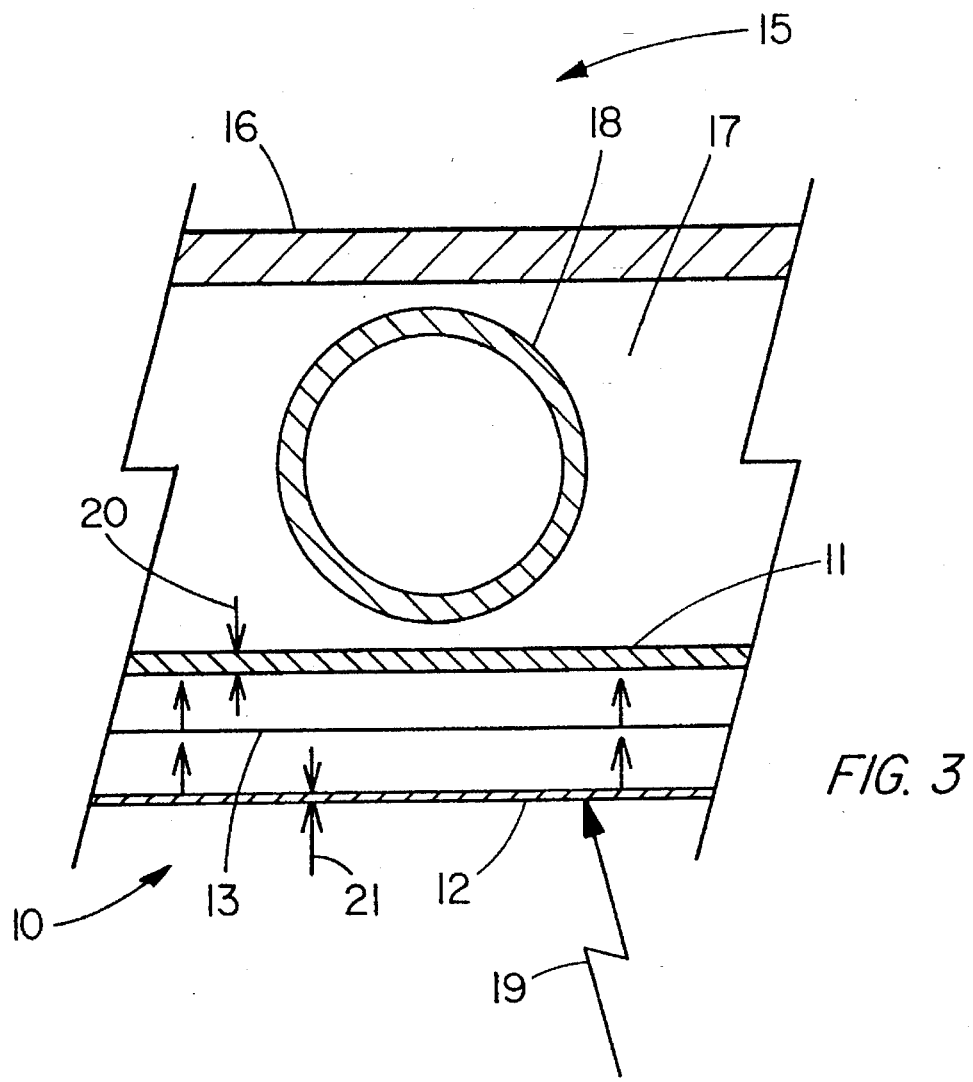
FIG. 3 depicts a further enlarged cross-sectional view of the container of FIG. 2.

FIG. 1 depicts an illustrative, preferred embodiment of ultraviolet light absorbing package or container 15 for containing sterile medical products such as guiding catheter 18 and for protecting the catheter from harmful ultraviolet light. Sterile medical products include any medical product that is injected, inserted, or introduced into a human or animal body or eye. Other medical products such as pharmaceuticals and the like that are subjected to less stringent pathogen-free or aseptic packaging requirements are also contemplated. Many sterile medical products such as guiding catheter 18 and other intravascular products are formed from and include a plastic or polymer material that is subject to oxidation and consequential deterioration when exposed to harmful ultraviolet light. Although the complete spectrum of ultraviolet light is contemplated, of major concern is ultraviolet light that has a wavelength in a range of from 285 to 358 nanometers. Oxidation and deterioration of the medical product results from the product being stored for extended periods of time, particularly when exposed to ultraviolet light emitted from the sun or fluorescent illumination. Such deterioration over extended periods of, for example, six months or more can render the medical product unsafe for use, particularly when inserted in the body of a human or animal patient.

Ultraviolet light absorbing container 15 includes an ultraviolet light absorbing transparent laminate 10 attached through heat sealing or other suitable form of encapsulation to sheet 16 of a commercially available spun-bonded olefin material which forms a cavity 17 therebetween for inserting the medical product therein. The cavity is defined by a heat seal 23 or other suitable form of encapsulation and extends around the entire periphery of the laminate 10 and the sheet 16 to hermetically encapsulate the cavity 17 and a medical product 18. The medical product 18 is inserted in the cavity and the package sealed for subsequent use. Commonly, the attached transparent laminate and sheet of spun-bonded olefin material are then subjected to a well-known sterilization process using, for example, an ethylene oxide gas sterilant. The ethylene oxide sterilant passes through the olefin material sheet of the container and sterilizes the medical product, as well as the inside of the container, from harmful microorganisms and particulate such as bacteria, spores, and the like.

Transparent packaging laminate 10 most effectively absorbs harmful ultraviolet light having a wavelength in a range of from 285 to 358 nanometers and protects the contained medical product from exposure to this harmful ultraviolet light and subsequent deterioration of the product. Samples of the laminate indicate all but approximately 6–7% of the ultraviolet light in the given range is absorbed. The transparent packaging laminate 10 allows the user easy visualization of the product and protects the product for periods of up to five or more years without harmful deterioration. A transparent material is one in which light of a given spectrum can pass therethrough so that distinct objects or images can still be perceived by the human eye. A translucent material is one in which light of a given spectrum can pass therethrough so that distinct objects or images can no longer be perceived by the human eye. Sheet 16 of the spun-bonded olefin material is a well-known and commercially available ultraviolet light opaque material such as TYVEK material, which is commercially available from E.I. DuPont de Nemours and Company. This spun-bonded olefin material readily transmits ethylene oxide gas and water vapor therethrough for sterilization of medical product 18. However, this material provides an effective barrier to microorganisms such as bacteria and the like.

FIG. 2 depicts a partially enlarged, cross-sectional view of container 15 and guiding catheter 18 of FIG. 1 taken along the line 2—2. This cross-sectional end view depicts guiding catheter 18 in cavity 17 of container 15 between ultraviolet light absorbing transparent laminate 10 and sheet 16 of spun-bonded olefin material 24. Ultraviolet light 19 incident on transparent packaging laminate 10 is absorbed by the laminate with the remaining spectrum of light 25 being transmitted therethrough for incidence on the medical product and sheet 16 of olefin material 24. Transparent packaging laminate 10 includes first transparent film 11 of a flexible carrier material, such as, for example, a synthetic polymer layer laminated to second transparent film 12 of an ultraviolet light absorbing material, such as, for example, a polyester.

FIG. 3 depicts a further enlarged cross-sectional view of container 15 and catheter 18 of FIG. 2. The view of the ultraviolet light absorbing transparent packaging laminate has been exploded to further depict transparent films 11 and 12 thereof with adhesive 13 for laminating the two transparent films together. Adhesive 13 is a commercially available polyester adhesive for laminating the polymeric and ultraviolet light absorbing polyester materials together.

First transparent film 11 of a flexible carrier material has a thickness 20 of approximately 0.038 mm and a water vapor transmission rate of less than 20 grams/m²/24 hours. The water vapor transmission rates of the films utilized herein were determined per the American Society of Testing and Materials (ASTM) test method and practice F1249 on commercially available Mocon Permatran test equipment. Preferably, polymeric material of the first transparent film 11 comprises a commercially available, flexible transparent polyethylene packaging material. This flexible polyethylene material is preferred not only for its low water vapor transmission rate of, for example, 12.4 to 13.95 grams/m²/24 hours, but it also exhibits residuals of ethylene oxide less than 250 ppm after ethylene oxide sterilization. Residuals of ethylene oxide less than 250 ppm are required to meet Federal Food and Drug Administration requirements. The low water vapor transmission rate of the polyethylene material resists water vapor penetration. Significant water vapor penetration of a packaging material can wrinkle the smooth transparent surfaces of the material and distort and alter the image of a medical product contained thereunder.

However, sheet 16 of the spun-bonded olefin material on the other side of the container has a significantly greater water vapor transmission rate for readily transmitting water vapor therethrough, which is needed in the ethylene oxide sterilization process. Since the olefin material is ultraviolet light opaque, the wrinkling of the material and the distortion of visual images therethrough is not of major concern. As also previously suggested, the spun-bonded olefin material has a thickness in a range of 0.18 to 0.25 mm and readily transmits ethylene oxide gas and water vapor therethrough for the ethylene oxide sterilization process.

Flexible, transparent polymeric materials other than polyethylene are available with a water vapor transmission rate of less than 20 grams/m²/24 hours for use as first transparent film. Suitable polymeric carrier materials are from a group consisting of commercially available polyvinylidene chloride, styrene, polyamides, polyether block amides, polyesters, and polyolefins. The styrene includes a butadiene styrene. The polyamides and the polyether block amides also include an ionomer film laminated thereto and formed from ethylene copolymers with methacrylic acid. The polyesters include polyesterterephthalate and polyesterterephthalate glycol modified. Polyethylene along with ethylene vinyl acetate is part of the group of polyolefins.

Classically, polymeric carrier materials such as polyethylene do not absorb or reflect harmful ultraviolet light, which can readily oxidize and deteriorate medical products such as guiding catheter 18 and the like. As a result, the second transparent film 12 of ultraviolet light absorbing polyester material is laminated to first transparent film 11. The ultraviolet light absorbing polyester material is commercially available as a dyed polyester film from Courtaulds Performance Films, Inc., Martinsville, Va. This dyed polyester film absorbs all but approximately 6 to 7% of ultraviolet light having a wavelength in the range of from 285 to 358 nanometers, which is incident on the film.

Figure 4:
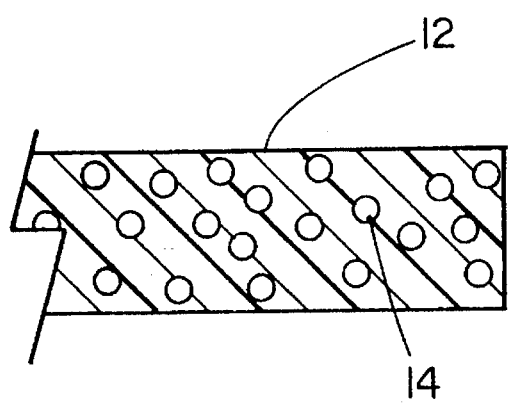
FIG. 4 depicts a transparent layer of dyed polyester material of FIG. 3 with dye contained therein.

FIG. 4 depicts transparent layer 12 of ultraviolet light absorbing polyester material of FIG. 3 with ultraviolet light absorbing material 14 in a matrix of polyester material. Ultraviolet light absorbing material 14 is from the chemical family of benzophenones. A preferred ultraviolet light absorbing material is methanone, bis(2-hydroxy-4-methoxyphenyl) of the chemical formula $C_{15}H_{14}O_5$. Another ultraviolet light absorbing material is 2.2'-dihydroxy-4.4'-dimethoxy-benzophenone. This preferred UV light absorbing material is also commercially available as UVINUL D-49 absorbing material from the BASF Corp., Parsippany, N.J.

As depicted in FIGS. 3 and 4, transparent film 12 absorbs ultraviolet light having a wavelength in a range of from 285 to 358 nanometers and has thickness 21 of approximately 0.013 mm. The dyed polyester film has a water vapor transmission rate greater than 20 grams/m²/24 hours. As a result, this ultraviolet light absorbing film transmits and absorbs water vapor and has a tendency to wrinkle. However, the lamination of this ultraviolet light absorbing transparent film to the polymeric transparent film with adhesive 13 unexpectedly produces a laminate which is substantially wrinkle free after ethylene oxide sterilization which requires various levels of humidity. A water vapor transmission rate of approximately 11.11 grams/m²/24 hours was obtained for the laminate at 100° F. and 90% relative humidity with the adhesive sealant towards or away from the moisture, respectively. In addition, the dyed polyester material exhibits residuals of ethylene oxide below 250 pm after ethylene oxide sterilization. Furthermore, laminate 10 exhibits residuals of ethylene oxide less than 250 ppm after ethylene oxide sterilization.

It is to be understood that the above-described ultraviolet light absorbing, transparent packaging laminate and medical product container containing such laminate is merely an illustrative embodiment of the principles of this invention and that other ultraviolet light absorbing or reflecting transparent laminates may be devised by those skilled in the art without departing from the spirit and scope of this invention. In summary, the ultraviolet light absorbing, transparent packaging laminate of the present invention represents a significant breakthrough in packaging material for protecting sterile medical products which are subject to ultraviolet light oxidation and resulting deterioration. The water vapor transmission rate and ultraviolet light absorbing properties of the laminate make this packaging material particularly suited for ethylene oxide sterilization in which high levels of humidity are encountered. Furthermore, the high water vapor transmission rate of the ultraviolet light absorbing, polyester film would suggest that the laminate would wrinkle and distort the visual appearance of the contained medical product. Unexpectedly, the laminate of the present invention is substantially wrinkle-free and presents a smooth surface for substantially distortion-free viewing of the product while still offering a high degree of ultraviolet light absorption. This ultraviolet light absorption protects medical products subject to oxidation and deterioration and extends its shelf life substantially. Prior to this, medical products such as guiding catheters and the like included large amounts of antioxidants and the like to combat the effects of ultraviolet light. However, the inclusion of these antioxidants significantly alter the properties of the catheter such as significantly and undesirably increasing the durometer and stiffness of the catheter. Furthermore, high concentration of these antioxidants also seriously affect the bonding property of the constituent materials which affect the safety and efficacy of the device.

The medical device 18 is packaged according to the invention by placing the medical device 18 between the transparent laminate 10 and the spun-bonded olefin sheet 16. The two sheets are then preferably sealed together through heat sealing around the entire periphery of the two sheets to define a cavity 17 with the medical device 18 positioned therein. The heat-sealing operation hermetically seals the medical device 18 within the cavity 17.

After the package has been thus formed, the package is treated in an ethylene oxide and water vapor atmosphere in a well known process to sterilize the cavity 17 and the medical device 18 therein. The ethylene oxide passes through the sheet 16 of spun-bonded olefin material and into the cavity 17 to sterilize the medical device 18. After the appropriate length of time, the ethylene oxide and water vapor atmosphere is removed and the package is then withdrawn from the ethylene oxide atmosphere. The ethylene oxide can then pass back through the sheet 16 to a point where the package contains less than 250 ppm of ethylene oxide.

What is claimed is:

1. An ultraviolet light absorbing, transparent packaging laminate (10) comprising:
   a first transparent film (11) having a first thickness (20) and a water vapor transmission rate of less than 20 grams/m$^2$/24 hours; and
   a second transparent film (12) comprising at least one of polyesterterephthalate and polyesterterephthalate glycol modified laminated to said first film, said second transparent film (12) having an ultraviolet light absorber material therein for absorbing ultraviolet light (19) having a wavelength in a given range, said second transparent film also having a second thickness (21) less than said first thickness and a water vapor transmission rate greater than 20 grams/m$^2$/24 hours, whereby said laminate is substantially wrinkle free after ethylene oxide sterilization.

2. The laminate of claim 1 wherein said laminate has residuals of ethylene oxide less than 250 ppm after ethylene oxide sterilization.

3. The laminate of claim 1 further comprising an adhesive (13) laminating said first transparent film and said second transparent film together.

4. The laminate of claim 1 wherein said first transparent film comprises a polymeric material (22) having residuals of ethylene oxide below 250 ppm after ethylene oxide sterilization.

5. The laminate of claim 1 wherein said ultraviolet light absorbing material includes a benzophenone (14).

6. The laminate of claim 1 wherein said first transparent film comprises a polymeric material selected from at least one of a group consisting of polyvinylidene chloride, polystyrene, polyamides, polyether block amides, polyesters, and polyolefins.

7. The laminate of claim 6 wherein said polystyrene includes a polybutadiene styrene.

8. The laminate of claim 7 wherein at least one of said polyamides and said polyether block amides includes an ionomer film laminated thereto and formed from ethylene copolymers with methacrylic acid.

9. The laminate of claim 6 wherein said polyolefins includes at least one of a group consisting of polyethylene and a polymer of ethylene vinyl acetate.

10. An ultraviolet light absorbing, medical product container (15) comprising:
    an ultraviolet light absorbing laminate (10) comprising a first transparent film (11) of a carrier material having a first thickness (20) and a water vapor transmission rate of less than 20 grams/m$^2$/24 hours and a second transparent film (12) of an ultraviolet light absorbing material laminated to said first transparent film of said carrier material, absorbing ultraviolet light (19) having a wavelength in a range of from 285 to 358 nanometers when incident thereon and having a water vapor transmission rate greater than 20 grams/m$^2$/24 hours, and
    a sheet (16) of a spun-bonded olefin material attached to said laminate, opaque to ultraviolet light and forming a cavity (17) therebetween for containing a medical product (18) therein, said sheet of spun-bonded olefin transmitting ethylene oxide gas therethrough and inhibiting transmission of microorganisms therethrough, whereby said laminate is substantially wrinkle free after ethylene oxide sterilization.

11. The container of claim 10 further comprising an adhesive (13) laminating said first transparent film of said carrier material and said second transparent film of said ultraviolet light absorbing material together.

12. The container of claim 11 wherein said carrier material comprises at least one of a group consisting of polyvinylidene chloride, styrene, polyamides, polyether block amides, polyesters, and polyolefins.

13. The container of claim 12 wherein said polyolefins includes at least one of a group consisting of polyethylene and ethylene vinyl acetate.

14. The container of claim 12 wherein said styrene includes a butadiene styrene.

15. The laminate of cliam 12 wherein at least one of said polyamides and said polyether block amides includes an ionomer film laminated thereto and formed from ethylene copolymers with methacrylic acid.

16. The container of claim 12 wherein said ultraviolet light absorbing material includes at least one of a group consisting of polyesterterephthalate and polyestesterephthalate glycol modified.

17. The container of claim 11 wherein said laminate has residuals of ethylene oxide less than 250 ppm after ethylene oxide sterilization.

18. An ultraviolet light absorbing, medical product container (15) comprising:
    an ultraviolet light absorbing laminate (10) comprising a first transparent film (11) of a flexible polyethylene material having a thickness (20) of approximately 0.038 mm and a water vapor transmission rate of less then 20 grams/m$^2$/24 hours and a second transparent film (12) of a polyester material having a thickness (21) of approximately 0.013 mm, laminated to said first transparent film of said flexible polyethylene material, absorbing ultraviolet light having a wavelength in a range of from 285 to 358 nanometers when incident thereon and having a water vapor transmission rate greater than 20 grams/m$^2$/24 hours; and
    a sheet (16) of a spun-bonded olefin material attached to said laminate, opaque to ultraviolet light and forming a cavity (17) therebetween for containing a medical product (18) therein, said sheet of said spun-bonded olefin material transmitting ethylene oxide gas therethrough and inhibiting transmission of microorganisms therethrough, whereby said laminate is substantially wrinkle free after ethylene oxide sterilization.

19. A method for packaging a medical device which is adversely affected by a given range of wavelengths of ultraviolet light comprising the steps of:
    placing the medical device between a pair of thermoplastic sheets;
    a transparent portion of at least one of the thermoplastic sheets absorbing incident ultraviolet light at least in the given range of wavelengths;
    a remainder of the thermoplastic sheets being opaque at least to ultraviolet light in the given range of wavelengths;
    at least one of the thermoplastic sheets further having at least a portion which is permeable to ethylene oxide gas and water vapor and characterized by a residual ethylene oxide content of less than 250 ppm after sterilization;

hermetically sealing the thermoplastic sheets around all of the medical device, the transparent portion and the permeable portion to hermetically encapsulate the medical device between a pair of thermoplastic sheets to thereby form a package with the medical device visible through the transparent portion;

passing ethylene oxide and water vapor through the permeable portion to sterilize the medical device within the package and to sterilize the interior of the package; and subsequently removing the ethylene oxide from the interior of the package.

20. A method for packaging a medical device according to claim 19 wherein the transparent portion comprises a first transparent thermoplastic film which has a water vapor transmission rate of less than 20 grams/m$^2$/24 hours and a second transparent thermoplastic film which is laminated to the first transparent film and is formed of an ultraviolet light absorbing polyester material having a water vapor transmission rate greater than 20 grams/m$^2$/24 hours.

21. A method for packaging a medical device according to claim 20 wherein the remainder of the thermoplastic sheets is a spun-bonded polyolefin and the permeable portion comprises at least a portion of the remainder of the thermoplastic sheets.

22. A method for packaging a medical device according to claim 20 wherein the first transparent thermoplastic film and the second transparent thermoplastic film are laminated together with a polyester adhesive.

23. A method for packaging a medical device according to claim 20 wherein the first transparent thermoplastic film is selected from the group consisting of polyvinylidene chloride, styrene, polyamide, polyether block amides, polyesters and polyolefins.

24. A method for making a medical device according to claim 23 wherein the second transparent film is an ultraviolet light absorbing polyester material selected from the group consisting of polyester terephthalate and polyester terephthalate glycol.

25. A method for packaging a medical device according to claim 19 wherein the remainder of the thermoplastic sheets is a spun-bonded polyolefin which is capable of transmitting ethylene oxide gas therethrough.

26. A method for packaging a medical device according to claim 19 wherein the step of removing the ethylene oxide gas from the interior of the package comprises the step of reducing the ethylene oxide in the package to less than 250 ppm.

27. A method of packaging a medical device according to claim 19 wherein the remainder of the thermoplastic sheets is translucent to visible light.

28. A medical package for a medical device which is adversely affected by a given range of wavelengths of ultraviolet light comprising:

a pair of thermoplastic sheets at least one of which has a transparent portion which is capable of absorbing ultraviolet light at least in the given range of wavelengths and a remainder of said thermoplastic sheets is opaque at least to ultraviolet light in the given range of wavelengths;

at least one of the thermoplastic sheets further having at least a portion which is permeable to ethylene oxide gas and water vapor;

a medical device which is adversely affected by a given range of wavelengths of ultraviolet light between the thermoplastic sheets and visible through the transparent portion;

a hermetic seal between the thermoplastic sheets around all of the medical device, the transparent portion and around the permeable portion to hermetically encapsulate the medical device between the pair of thermoplastic sheets to thereby form a package with the medical device visible through the transparent portion;

the interior of the package, including the medical device, being sterile;

at least the permeable portion of the thermoplastic sheets having a residual ethylene oxide content of less than 250 ppm.

29. A medical package according to claim 28 wherein the interior of the package is sterilized by passing ethylene oxide and water vapor through the permeable portion.

30. A medical package according to claim 28 wherein the transparent portion comprises a first transparent thermoplastic film which has a water vapor transmission rate of less than 20 grams/m$^2$/24 hours and a second transparent thermoplastic film which is laminated to the first transparent film and is formed of an ultraviolet light absorbing polyester material having a water vapor transmission rate of greater than 20 grams/m$^2$/24 hours.

31. A medical package according to claim 30 wherein the remainder of the thermoplastic sheets is a spun-bonded polyolefin and the permeable portion comprises at least a portion of the remainder of the thermoplastic sheets.

32. A medical package according to claim 30 wherein the first transparent thermoplastic film and the second transparent thermoplastic film are laminated together with a polyester adhesive.

33. A medical package according to claim 30 wherein the first transparent thermoplastic film is selected from the group consisting of polyvinyl chloride, styrene, polyamide, polyether block amides, polyesters and polyolefins.

34. A medical package according to claim 33 wherein the second transparent film is an ultraviolet light absorbing polyester material selected from the group consisting of polyester terephthalate and polyester terephthalate glycol.

35. A medical package according to claim 28 wherein the remainder of the thermoplastic sheets is a spun-bonded polyolefin which is capable of transmitting ethylene oxide gas therethrough.

36. A medical package according to claim 28 wherein the remainder of the thermoplastic sheets is translucent to visible light.

* * * * *